United States Patent [19]

Mayes

[11] Patent Number: 4,683,911
[45] Date of Patent: Aug. 4, 1987

[54] FLUID PROPORTIONING DEVICE
[75] Inventor: Ronald A. Mayes, Beaumont, Tex.
[73] Assignee: Helena Laboratories, Beaumont, Tex.
[21] Appl. No.: 817,004
[22] Filed: Jan. 8, 1986
[51] Int. Cl.⁴ ............................................. C12M 1/00
[52] U.S. Cl. ................................ 137/561 A; 435/296; 137/561 R
[58] Field of Search ...................... 137/561 A, 561 R; 141/237, 242, 244; 435/296, 810

[56] References Cited

U.S. PATENT DOCUMENTS

| | | | |
|---|---|---|---|
| 2,056,191 | 10/1936 | Peltz | 141/237 |
| 2,148,414 | 2/1939 | Wolfert et al. | 137/561 A X |
| 2,193,696 | 3/1940 | Ramsaur | 137/561 A X |
| 3,103,942 | 9/1963 | Sharp | 137/561 R X |
| 3,169,098 | 2/1965 | Leavitt | 137/561 R X |
| 3,640,308 | 2/1972 | Bydal | 137/561 A X |
| 3,776,269 | 12/1973 | Watts | 137/561 A |
| 4,283,498 | 8/1981 | Schlesinger | 435/296 |
| 4,284,243 | 8/1981 | Shaner | 137/561 A |
| 4,487,223 | 12/1984 | Davies | 137/561 R |
| 4,512,368 | 4/1985 | Kaminaka et al. | 137/561 A |

Primary Examiner—Alan Cohan
Assistant Examiner—John A. Rivell
Attorney, Agent, or Firm—Phillips, Moore, Lempio & Finley

[57] ABSTRACT

A fluid proportioner is disclosed that will divert a volume of fluid to two or more containers in relatively equal amounts without the necessity of measuring or weighing the fluid to accomplish division. The proportioner consists of tubular member ending in a closure. Two additional smaller tubular members extend into the larger tubular member. These two smaller members have ends interior of the first tubular member that are cut on an angle.

6 Claims, 2 Drawing Figures

FLUID PROPORTIONING DEVICE

FIELD OF THE INVENTION

This invention relates to a fluid proportioner. In particular it relates to a fluid proportioner useful in the medical arts for dividing into relatively equal parts fluid samples obtained from or passed by mammals and particularly samples obtained from humans.

BACKGROUND OF THE INVENTION

In the medical and veterinary fields bodily fluid samples such as urine are quite frequently obtained to assist in the diagnosis of ailments. Since this invention is particularly useful in the medical field it will be discussed in that context, however, it should be understood that it is applicable to the veterinary field. On occasion a fluid sample, such as a urine sample procured over a 24 hour period, could be used for several things. Initially, it may be important to determine the volume of fluid passed by the individual during a 24-hour period. Secondly, body fluid, such as urine obtained over a 24 hour period, may be helpful in determining the presence of an ailment such as diabetes and the like. It is also common that more than one test may be performed on the 24 hour fluid sample. While it would be possible to divide the sample after it is fully obtained from the patient, certain tests require different preservatives in order to maintain the fluid in condition for testing. If the preservatives in each of the tests were identical, then division of the sample at the end of the 24 hour period would be simple. Since preservatives quite frequently are mutually exclusive division of the sample after collection is precluded unless a third container is used for collection and immediate division.

Because of the mutual exclusivity of the preservatives used in 24 hour collection tests, it is common practice for physicians when obtaining urine, to require a patient to collect fluid not over a 24-hour period but over a 48-hour period. While this provides the physician with the necessary samples for testing, it works an inconvenience on the patient in that the patient's movements are restricted for twice the period of time.

It might be suggested that the urine be divided at the time the sample is passed. This could be a workable solution if the patient could always be relied upon to divide the sample obtained at each passing such that one half was placed in one collection bottle and the other half placed in a second collection bottle. In the hospital situation where the patient provides the sample to a nurse, the physician is dependent upon the nurse to divide the sample throughout the 24-hour period. While this seems to be a viable solution from the standpoint of the nursing profession, it is still subject to human error thus an entire sample may have to be discarded if a descrepancy occurs during the sampling.

Accordingly, this invention provides a simple inexpensive fluid proportioner which may be used in association with 24 hour body fluid sample.

It is a further object of the invention to provide a fluid proportioner that may be utilized to divide samples into two relatively equal sample sizes over an elapsed period of time.

It is still a further object of this invention to provide a fluid proportioner that is inexpensive.

It is still a further object of this invention to provide a fluid proportioner that will withstand the hostile environment of a sterilization process.

It is also an object of this invention to provide a fluid proportioner that may be used in conjunction with standard sample containers and funnels.

The invention is a fluid proportioner that includes a first tubular member having an open end and a closed end. At least two second tubular members each having a cross sectional area less than the cross sectional area of the first tubular member are affixed to and open into the closed end of the first tubular member.

DETAILED DESCRIPTION OF THE PREFERRED EMBODIMENT

Figure 1:
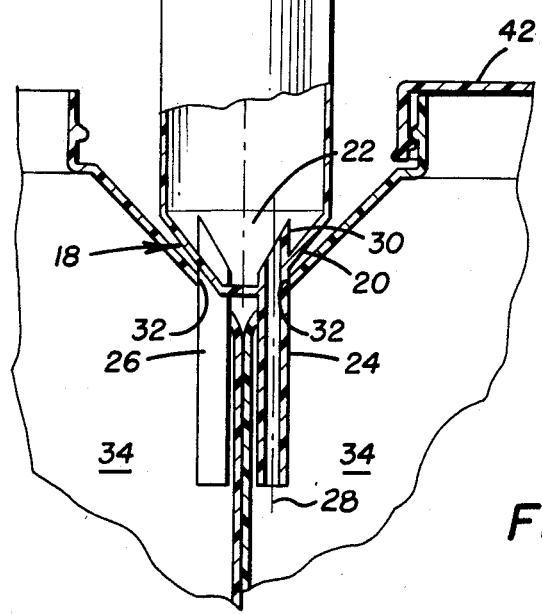
FIG. 1 is a view partially in section of the fluid proportioner that forms an object of this invention.

Referring now to FIG. 1, fluid proportioner 10 as illustrated includes a first tubular member 12 defining an axis 14. First tubular member 12 is preferably circular in cross-section, however, a polygonal shape would serve equally as well. In certain instances where fluids are divided into more than two containers, the cross-section may be in the form of a triangle, or a, regular polygon having the number of sides equal to the number of desired samples. More will be said about this in ensuing discussion.

First tubular member 12 is formed with an open-end 16 and a closed end 18 preferably of a sterilizable material such as one of the plastics that may be injection molded. Closed end 18 is formed with converging sidewalls 20 so that a volume 22 is formed by the closed end of tubular member 12. Volume 22 has a decreasing cross section as the converging side walls 20 approach axis 14. It may be appropriate to truncate closed end 18 as shown in FIG. 1. This will result in less residual sample staying in tubular member 12 during use.

In the embodiment illustrated in FIG. 1, there are two second tubular members 24 and 26. Each of the second tubular members extends through the closed end of the first tubular member. In addition the second tubular members are permanently affixed and preferably are molded with first tubular member 12. Each tubular member 24 and 26 defines an axis 28 which is substantially parallel to and offset from axis 14. For convenience, since tubular member 24 is identical to tubular member 26 except in one respect, the discussion will be directed to the structure of the one tubular member 24. It should be understood that the other tubular member 26 has in an identical shape except for the portion interior of first tubular member 12.

Figure 2:
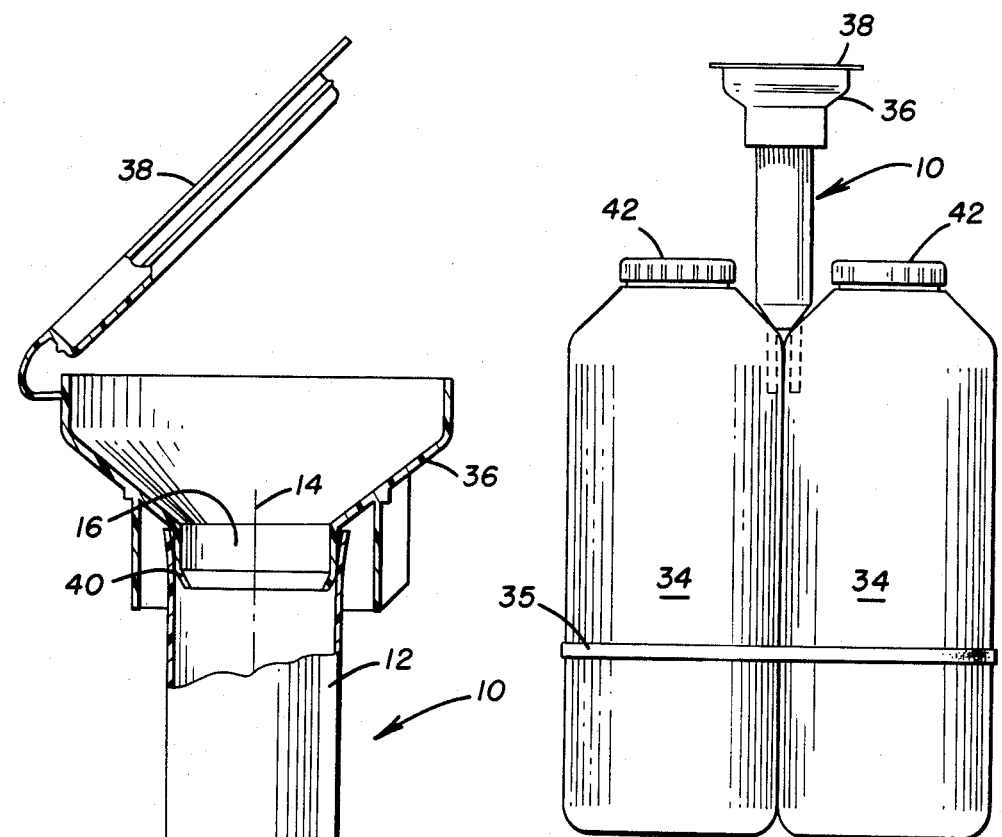
FIG. 2 is the same fluid proportioner shown in FIG. 1 but shown in conjunction with the fluid sample collectors.

As previously noted second tubular member 24 extends through closed end 18 of tubular member 12. The second tubular member 24 extends into volume 22 a relatively short distance as indicated in FIG. 2 and preferably only into volume 22. The end 30 of second tubular member 24 which opens into volume 22 cut at an angle to axis 28. The preferred angle is between 15 and 75 degrees and generally runs parallel to the angle of the converging sidewall 20. Thus if converging sidewall 20 is at an angle of 30°, the end 30 of second tubular member 26 would also be at 30°. The other ends of second tubular members 24 and 26 are elongated as indicated in FIG. 1 to the extent that each of the tubular members may be passed through an opening 32 in a sample collection containers 34.

The sample collection containers 34, as indicated in FIG. 2, would generally be in the nature of a one to one-and-a half liter plastic container which may be fixed together by an elastic band 36. Such sample containers are readily available in the market place and need not be further discussed except in combination with fluid proportioner. It may be necessary, however, to pre-drill the commercially available sample collection bottles 34 so that when the two collection bottles are positioned in the manner shown in FIG. 2 the holes 32 bored in the containers 34 are located so that the second tubular members may be readily passed through the holes 32. Further modification of the container, in the form of locking type slots to insure the two containers remained juxtaposed is also possible. Finally some sort of closure to holes 32 may also be included.

Since the fluid proportioner 10 may have a cross-sectional area in the neighborhood of only two to three centimeters, it may be appropriate to utilize a funnel 36 in conjunction with open-end 16. Funnels, such as funnel 36, are readily available in the marketplace, however, it would be appropriate to utilize a cover 38 on funnel 36 so that odors associated with the collected sample are contained within the sample containers and further so that air borne contaminants do not settle within the first tubular member 12 to be subsequently washed into the sample during the collection process. Funnel 36 should be formed so that its smaller end 40 will readily fit into first tubular member 12.

Finally, sample collection bottles 40 should be equipped with covers 42 again in a conventional manner.

OPERATION OF THE PREFERRED EMBODIMENT

It should be apparent to one skilled in the art how the fluid proportioner operates, however the following comments are offered in clarification of this specification.

First, the sample containers 34 should be prepared for use by the laboratory. This may entail providing each bottle 34 with appropriate chemicals to be utilized in the test and possibly also to preserve the fluid being collected. The covers 42 may be formed so that identification of the patient and the test to be performed may be readily inscribed on the top. This may be accomplished by the usual frosting of the plastic cover 42. Likewise, the cover 38 of funnel 36 should also identify the patient so that the likelihood of mixing the samples is lessened.

The fluid proportioner 12 should then be placed in the sample containers 34 with the sample containers in the juxtaposed position as shown in FIG. 2 and the elastic band 35 holding the bottles together. It has been found that the tubular members 32 when inserted in the containers 34 and the elastic band 35 in place, a relatively rigid package of the fluid proportioner and the two sample collection containers is obtained.

It is not envisioned that the patient, upon whom the test is being performed, will void directly into the funnel 36 although this is not necessarily precluded, rather is is envisioned that the sample will be collected each time the patient voids fluid into a single collection container. The collected sample is then transferred into the first tubular member 12 through funnel 36. It has been found that when the ends of second tubular members 24 and 26 interior of volume 22, are formed at an angle, as shown in FIG. 1, the fluid passed into first tubular member 12 is proportioned relatively equally between the two sample collection bottles 34. Experimentation has shown that when this angle is between 15° and 75°, the volumes of fluid proportioned between the two sample containers is within 5%. Without the bevel, air pockets form in the tubular members resulting in extreme errors.

By truncating closed end 18 and limiting the penetration of second tubular members 24 and 26 to no more than volume 22 along with the angled ends of members 24 and 26 reduces residual fluid remaining in member 12 to a few milliliters.

At the end of the 24-hour period, the fluid proportioner 10 may be withdrawn from the two sample collection bottles 34 and the holes 32 closed or covered with tape or the like. The bottles 34 may then be delivered to the laboratory for appropriate testing. Fluid proportioner 10, having been made out of a relatively cheap plastic, may be discarded along with the funnel 36.

As noted early in the specification, the particular embodiment described herein is based on two sample collection bottles and a fluid proportioner 10 having a circular cross-section. If multiple collection bottles 34 are used then the cross-section of fluid proportioner 10 may take the form of a regular polygon such as a triangle, a square, or a pentagon as appropriate. In that instance there would be three, four, or five tubular members equivalent to second tubular members 24 and 26 to fit into the three, four, or five sample collection bottles 34.

While this invention has been described with respect to a preferred and alternative embodiments, it is emphasized that the invention should not be so restricted but rather should be construed in light of the claims appended hereto.

What is claimed is:

1. A fluid proportioner comprising:
   an elongation first tubular member having an open-end and a closed-end forming a single cavity therein, said first tubular member defining a first longitudinal axis, wherein the closed-end of said elongated first tubular member is formed with sidewalls converging at an acute angle to said first-longitudinal axis;
   at least two elongated second tubular members each having a cross-sectional area less than the cross-sectional area of the first tubular member, said at least two second tubular members affixed to, extending and opening into the converging closed-end of the first tubular member, each of said elongated second tubular members defining a second longitudinal axis throughout its entire length, each said second longitudinal axis substantially parallel to the first longitudinal axis, and further wherein the ends of the at least two second tubular members interior of the first tubular member are cut at an angle acute to the second longitudinal axis and generally equal to the angle of convergence of the sidewalls of the first tubular member.

2. The fluid proportioner of claim 1 wherein the angle of the cut of the second tubular member is between 15° and 75° to the axis of the second tubular member.

3. The fluid proportioner of claim 2 wherein the at least two second tubular members extend only into the volume formed by the closed end of the first tubular member.

4. The fluid proportioner of claim 1 further including a frustoconical funnel member, the smaller end of said frustoconical member having an integrally formed third tubular member having an outside dimension less than the inside dimension of said first tubular member.

5. The fluid proportioner of claim 4 wherein said funnel member further includes an openable closure for the larger end of said frustoconical member.

6. In Combination with at least two collection bottles a fluid proportioner or comprising:
- an elongated first tubular member having an open-end and a closed-end forming a single cavity therein, said first tubular member defining a first longitudinal axis, wherein the closed-end of said elongated first tubular member is formed with sidewalls converging at an acute angle to said first-longitudinal axis;
- at least two elongated second tubular members each having a cross-sectional area less than the cross-sectional area of the first tubular member, said at least two second tubular members affixed to, extending and opening into the converging closed-end of the first tubular member, each of said elongated second tubular members defining a second longitudinal axis throughout its entire length, each said second longitudinal axis substantially parallel to the first longitudinal axis, and further wherein the ends of the at least two second tubular members interior of the first tubular member are cut at an angle acute to the second longitudinal member and generally equal to the angle of convergence of the sidewalls of the first tubular member;
- each of said at least two elongated second tubular members insertable into one of said collection of bottles; and
- a frustoconical funnel member, the smaller end of said frustoconical funnel member having an integrally formed third tubular member defining an outside dimension less than the inside dimension of said first tubular member, said frustoconical funnel member formed to fit in the open-end of the first tubular member, said funnel member further including a openable closure for the larger end of the frustoconical member.

* * * * *